United States Patent [19]

Protonantis

[11] Patent Number: 5,762,079
[45] Date of Patent: Jun. 9, 1998

[54] PORTABLE FLOSS DISPENSING SYSTEM

[76] Inventor: Peter Protonantis, 435 Van Sicklen St., Brooklyn, N.Y. 11223

[21] Appl. No.: 754,793

[22] Filed: Nov. 21, 1996

[51] Int. Cl.$^6$ ............................................. A61C 15/00
[52] U.S. Cl. ..................... 132/325; 132/324; 132/323; 132/326
[58] Field of Search ......................... 132/323, 324, 132/325, 326, 327, 328, 309; 206/368, 635; 220/338, 337, 4.22

[56] References Cited

U.S. PATENT DOCUMENTS 4,753,254  6/1988  McCullough et al. .................. 132/324
5,159,943  11/1992  Richards et al. ........................ 132/323
5,415,187  5/1995  Heneveld ................................ 132/324

*Primary Examiner*—Gene Mancene
*Assistant Examiner*—Philogene Pedro

[57] ABSTRACT

A new Portable floss Dispensing System for dispensing floss conveniently from a portable storage device which prevents the floss from becoming unwound. The inventive device includes an elongated U-shaped member capped at one end by a closing end, a swaged elongated member, a conical guide receiving the floss, then a first and second support brace which guide the floss, and a conical floss securing member secured to the second support brace and securing the floss.

13 Claims, 3 Drawing Sheets

PORTABLE FLOSS DISPENSING SYSTEM

BACKGROUND OF THE INVENTION

1. Field of the Invention

The present invention relates to Dental Floss Devices and more particularly pertains to a new Portable Floss Dispensing System for dispensing floss conveniently from a portable storage device which prevents the floss from becoming unwound.

2. Description of the Prior Art

The use of Dental Floss Devices is known in the prior art. More specifically, Dental Floss Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Dental Floss Devices include U.S. Pat. No. 5,406,965; U.S. Pat. No. 5,415,188; U.S. Pat. Design No. 354,154; U.S. Pat. No. 5,280,797; U.S. Pat. No. 5,287,865 and U.S. Patent Design No. 350,624.

While these devices fulfill their respective, particular objectives and requirements, the aforementioned patents do not disclose a new Portable Floss Dispensing System. The inventive device includes an elongated U-shaped member capped at one end by a closing end, a swaged elongated member pivotally secured to the elongated U-shaped member opposite of the closing end, a floss spool rotatably secured to the elongated U-shaped member, a conical guide receiving the floss, then a first and second support brace which guide the floss, and a conical floss securing member secured to the second support brace and securing the floss.

In these respects, the Portable Floss Dispensing System according to the present invention substantially departs from the conventional concepts and designs of the prior art, and in so doing provides an apparatus primarily developed for the purpose of dispensing floss conveniently from a portable storage device which prevents the floss from becoming unwound.

SUMMARY OF THE INVENTION

In view of the foregoing disadvantages inherent in the known types of Dental Floss Devices now present in the prior art, the present invention provides a new Portable Floss Dispensing System construction wherein the same can be utilized for dispensing floss conveniently from a portable storage device which prevents the floss from becoming unwound.

The general purpose of the present invention, which will be described subsequently in greater detail, is to provide a new Portable Floss Dispensing System apparatus and method which has many of the advantages of the Dental Floss Devices mentioned heretofore and many novel features that result in a new Portable Floss Dispensing System which is not anticipated, rendered obvious, suggested, or even implied by any of the prior art Dental Floss Devices, either alone or in any combination thereof.

To attain this, the present invention generally comprises an elongated U-shaped member capped at one end by a closing end, a swaged elongated member pivotally secured to the elongated U-shaped member opposite of the closing end, a floss spool rotatably secured to the elongated U-shaped member, a conical guide receiving the floss, then a first and second support brace which guide the floss, and a conical floss securing member secured to the second support brace and securing the floss.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other, structures, methods and systems for carrying out the several purposes of the present invention. It is important, therefore, that the claims be regarded as including such equivalent constructions insofar as then do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Portable Floss Dispensing System apparatus and method which has many of the advantages of the Dental Floss Devices mentioned heretofore and many novel features that result in a new Portable Floss Dispensing System which is not anticipated, rendered obvious, suggested, or even implied by any of the prior art Dental Floss Devices, either alone or in any combination thereof.

It is another object of the present invention to provide a new Portable Floss Dispensing System which may be easily and efficiently manufactured and marketed.

It is a further object of the present invention to provide a new Portable Floss Dispensing System which is of a durable and reliable construction.

An even further object of the present invention is to provide a new Portable Floss Dispensing System which is susceptible of a low cost of manufacture with regard to both materials and labor, and which accordingly is then susceptible of low prices of sale to the consuming public, thereby making such Portable Floss Dispensing System economically available to the buying public.

Still yet another object of the present invention is to provide a new Portable Floss Dispensing System which provides in the apparatuses and methods of the prior art some of the advantages thereof, while simultaneously overcoming some of the disadvantages normally associated therewith.

Still another object of the present invention is to provide a new Portable Floss Dispensing System for dispensing floss conveniently from a portable storage device which prevents the floss from becoming unwound.

Yet another object of the present invention is to provide a new Portable Floss Dispensing System which includes an elongated U-shaped member capped at one end by a closing end, a swaged elongated member pivotally secured to the elongated U-shaped member opposite of the closing end, a floss spool rotatably secured to the elongated U-shaped member, a conical guide receiving the floss, then a first and second support brace which guide the floss, and a conical floss securing member secured to the second support brace and securing the floss.

Still yet another object of the present invention is to provide a new Portable Floss Dispensing System that dispenses dental floss for utilization by a user.

Even still another object of the present invention is to provide a new Portable Floss Dispensing System that eliminates floss from becoming loose and entangled within various other transported items.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
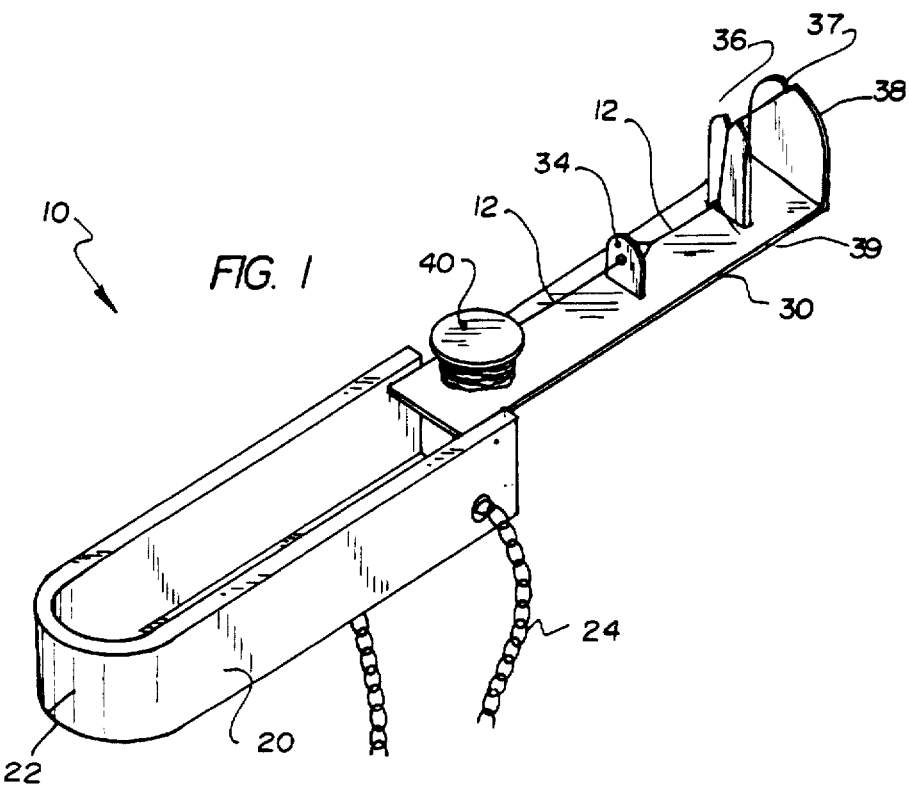
FIG. 1 is a perspective view of a new Portable Floss Dispensing System according to the present invention.
Figure 2:
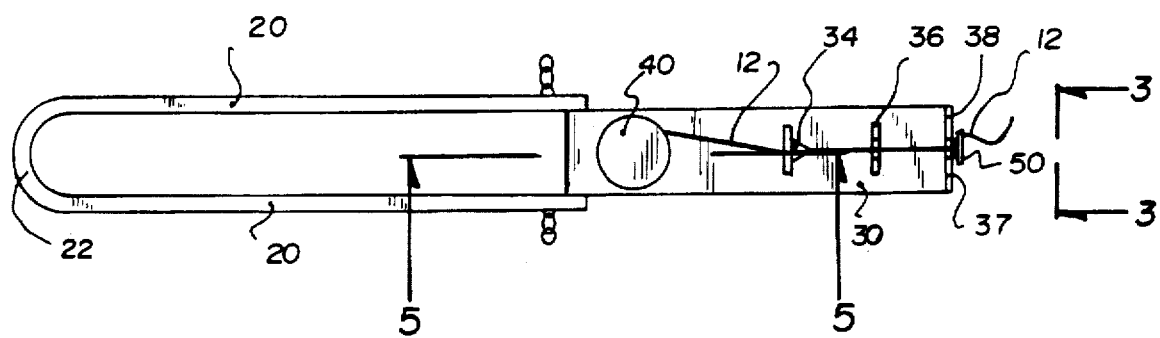
FIG. 2 is a top view thereof.

With reference now to the drawings, and in particular to FIGS. 1 through 6 thereof, a new Portable Floss Dispensing System embodying the principles and concepts of the present invention and generally designated by the reference numeral 10 will be described.

More specifically, it will be noted that the Portable Floss Dispensing System 10 comprises an elongated U-shaped member 20, a closing end member 22 secured to an end of the elongated U-shaped member 20, and a swaged elongated member 30 pivotally secured at one end to the end of the elongated U-shaped member 20 opposite of the closing end member 22, wherein the swaged elongated member 30 when folded encloses the space with in the elongated U-shaped member 20 forming an enclosed rectangular shaped box.

Figure 3:
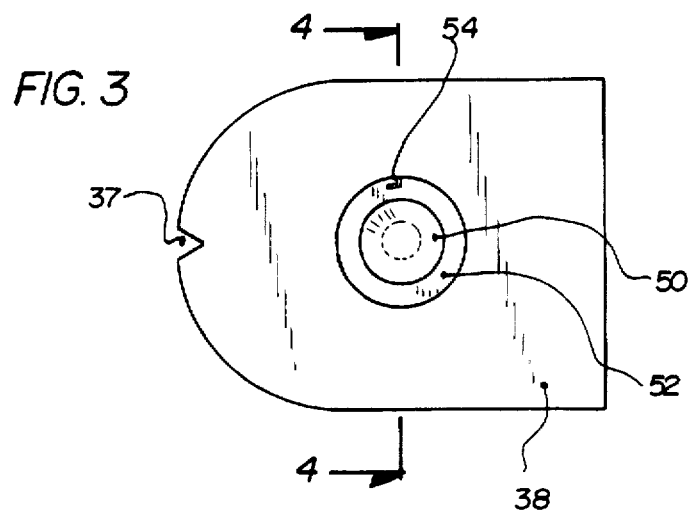
FIG. 3 is an cross sectional view taken along line 3—3 of FIG. 2.
Figure 4:
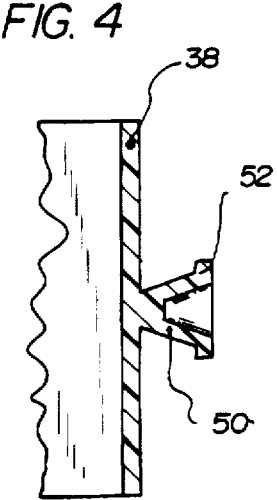
FIG. 4 is a cross sectional view taken along line 4—4 of FIG. 3.
Figure 5:
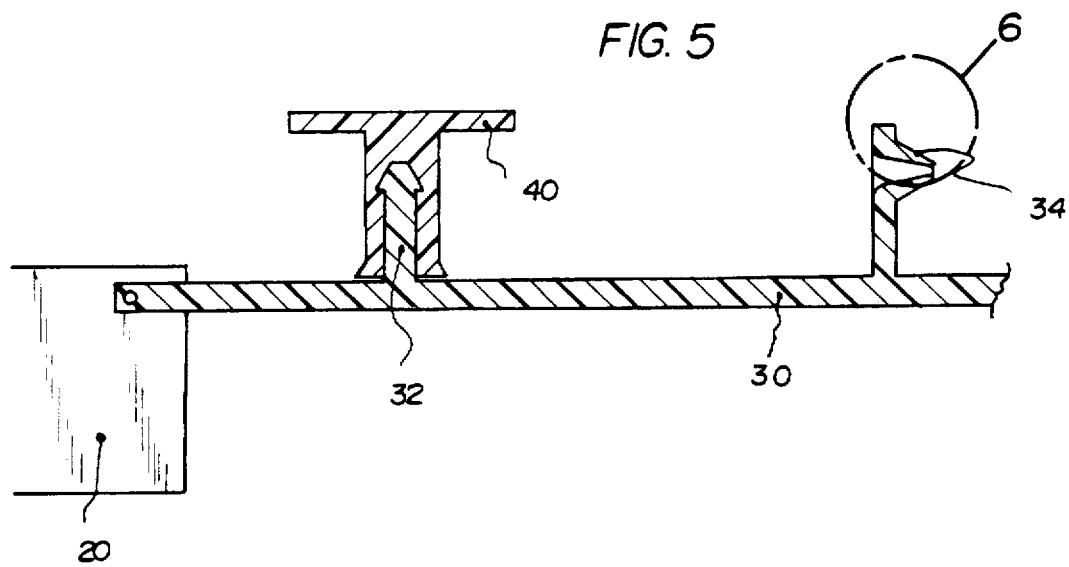
FIG. 5 is a cross sectional view taken along line 5—5 of FIG. 2.
Figure 6:
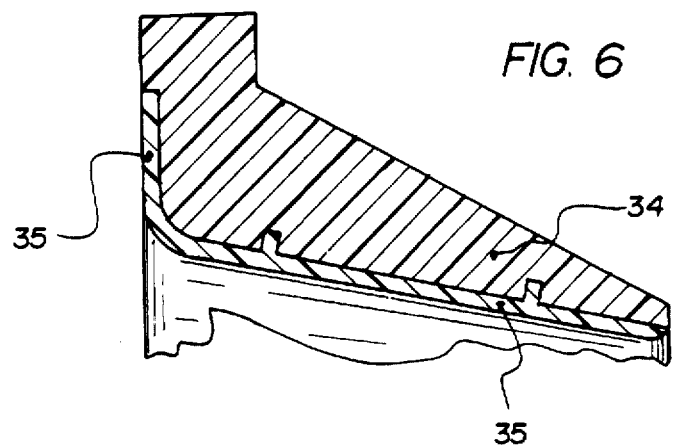
FIG. 6 is a magnified view of the conical guide from FIG. 5.

As best illustrated in FIG. 5, it can be shown that the swaged elongated member 30 includes a floss axle 32 secured orthogonally to the top surface. A conical guide 34 is secured centrally with the narrower portion projecting away from the floss axle 32. A second support brace 38 is secured orthogonally to the end opposite of the elongated U-shaped member 20. A first support brace 36 is secured orthogonally near the end opposite of the elongated U-shaped member 20. The first support brace 36 includes a floss aligning hook 39 adjacent to the swaged elongated member 30 as best shown in FIG. 1 of the drawings. The first support brace 36 includes a syncline notch 37 on the cornice as best shown in FIG. 1 of the drawings. The second support brace 38 includes another syncline notch 37 on the cornice as best shown in FIG. 3 of the drawings. The second support brace 38 includes a conical floss securing member 50 secured orthogonally to the surface opposite of the first support brace 36 as best disclosed in FIG. 2 through 4 of the drawings. The conical floss securing member 50 includes a flange 52 at the end opposite of the second support brace 38 as shown in FIG. 4 of the drawings. The flange 52 includes a floss securing notch 54. A floss spool 40 is rotatably mounted onto the floss axle 32. The conical guide 34 includes a nylon layer 35 in the central portion thereby reducing the resistance of floss flowing through. As best shown in FIG. 1 of the drawings, a length of floss 12 from the floss spool 40 projects horizontally through the conical guide 34, then through the floss aligning hook 39. The floss 12 then projects vertically along the surface of the first support brace 36, through the syncline notch 37 within the first support brace 316 horizontally to the syncline notch 37 within the second support brace 38. The floss 12 then slanted projects towards the conical floss securing member 50 and wound about said conical floss securing member 50. The lead end of the floss 12 removably terminates into the floss securing notch 54. The elongated U-shaped member 20 preferably includes a carrying chain 24 secured near the end pivotally securing the swaged elongated member 30 for carrying the present invention as shown in FIG. 1 of the drawings.

In use, the user opens the present invention by pivotally removing the swaged elongated member 30 from within the elongated U-shaped member 20, thereby exposing the interior components of the present invention. The user then grasps the lead end of the floss 12 secured to the floss securing notch 54 and removes a length of floss 12 required. The swaged elongated member 30 is then pivotally closed into the elongated U-shaped member 20 to form a compact elongated rectangular box shape which can be easily and conveniently inserted into the user's pocket for later utilization.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A portable floss dispensing system comprising:

a elongated U-shaped member;

a closing end member secured to and end of the elongated U-shaped member; and a swaged elongated member pivotally secured to the end of the elongated U-shaped member opposite of the closing end member, wherein the swaged elongated member when folded encloses the space within the elongated U-shaped member forming an enclosed rectangular shaped box;

a floss axle secured orthogonally to a top surface;

a conical guide secured centrally with a narrower portion projecting away from the floss axle;

a second support brace secured orthogonally to the end opposite of the elongated U-shaped member; and a first support brace secured orthogonally near the end opposite of the elongated U-shape member.

2. The portable floss dispensing system of claim 1, wherein:

the first support brace including a floss aligning hook adjacent to the swaged elongated member;

the first support brace including a syncline notch on a cornice;

the second support brace including a second support brace notch on a second support brace top surface; and the second support brace including a conical floss securing member secured orthogonally to the surface opposite of the first support brace.

3. The portable floss dispensing system of claim 2, wherein the conical floss securing member includes:

a flange at the end opposite of the second support brace; and the flange including a floss securing notch.

4. The portable floss dispensing system of claim 3, wherein a floss spool is rotatably mounted onto the floss axle.

5. The portable floss dispensing system of claim 4, wherein the conical guide includes a nylon layer in a central portion thereby reducing the resistance.

6. The portable floss dispensing system of claim 5, wherein a length of floss from the floss spool projects horizontally through the conical guide, then through the floss aligning hook, then vertically along the surface of the first support brace, through the syncline notch within the first support brace, horizontally to the syncline notch within the second support brace, then slanted toward the conical floss securing member and wound about said conical floss securing member, and terminating into the floss securing notch.

7. The portable floss dispensing system of claim 6, wherein the elongated U-shaped member includes a carrying chain secured near the end pivotally securing the swaged elongated member.

8. A portable floss dispensing system comprising:

an elongated U-shaped member;

a closing end member secured to an end of the elongated U-shape member;

an elongated member pivotally secured to the end of the elongated U-shape member opposite of the closing end member;

wherein the elongated member when folded encloses the space within the elongated U-shaped member forming an enclosed rectangular shaped box;

a floss axle secured orthogonally to a top surface of the elongated member;

a conical guide secured centrally with an narrower portion of the conical guide projecting away from the floss axle;

a second support brace secured orthogonally to the end of the elongated member opposite of the elongated U-shape member; and a first support brace secured orthogonally near the end of the elongated member opposite of the elongated U-shaped member.

9. The portable floss dispensing system of claim 8, wherein:

the first support brace includes a floss aligning hook adjacent to the elongated member;

the first support brace including a first support brace notch on a first support brace top surface;

the second support brace including a second support brace notch on a second support brace top surface; and the second support brace including a conical floss securing member secured orthogonally to the surface opposite of the first support brace.

10. The portable floss dispensing system of claim 9, wherein the conical floss securing member includes:

a flange at the end opposite of the second support brace; and the flange including a floss securing notch.

11. The portable floss dispensing system of claim 10, wherein a floss spool is rotatably mounted onto the floss axle.

12. The portable floss dispensing system of claim 11, wherein the conical guide includes a nylon layer in a central portion of the conical guide thereby reducing the resistance between the conical guide and the floss.

13. The portable floss dispensing system of claim 12, wherein a length of floss from the floss spool projects horizontally through the conical guide, then through the floss aligning hook, then vertically along the surface of the first support brace, through the first support brace not notch within the first support brace, horizontally to the second support brace notch within the second support brace, then slanted toward the conical floss securing member and wound about said conical floss securing member, and terminating into the floss securing notch.

* * * * *